(12) United States Patent
Jackels

(10) Patent No.: US 8,485,347 B2
(45) Date of Patent: Jul. 16, 2013

(54) APPARATUS AND METHOD FOR RECEIVING AND TRANSFERRING SOLID MATERIAL

(75) Inventor: Hans Adolf Jackels, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 273 days.

(21) Appl. No.: 13/089,414

(22) Filed: Apr. 19, 2011

(65) Prior Publication Data

US 2011/0253511 A1 Oct. 20, 2011

(30) Foreign Application Priority Data

Apr. 20, 2010 (EP) .................................. 10160396

(51) Int. Cl.
*B29C 65/00* (2006.01)

(52) U.S. Cl.
USPC ................ 198/689.1; 198/493; 198/550.1; 156/552

(58) Field of Classification Search
USPC ............ 198/689.1, 429, 493, 550.1; 156/552, 156/556, 276; 19/296
See application file for complete search history.

(56) References Cited

U.S. PATENT DOCUMENTS

| | | | | |
|---|---|---|---|---|
| 4,437,294 A | * | 3/1984 | Romagnoli | 53/553 |
| 4,715,918 A | * | 12/1987 | Lang | 156/273.1 |
| 5,030,314 A | * | 7/1991 | Lang | 156/390 |
| 5,494,622 A | * | 2/1996 | Heath et al. | 264/40.1 |
| 5,552,012 A | * | 9/1996 | Morris et al. | 156/272.4 |
| 5,607,760 A | | 3/1997 | Roe | |
| 5,609,587 A | | 3/1997 | Roe | |
| 5,635,191 A | | 6/1997 | Roe et al. | |
| 5,643,588 A | | 7/1997 | Roe et al. | |
| 6,330,735 B1 | * | 12/2001 | Hahn et al. | 19/296 |
| 6,802,834 B2 | * | 10/2004 | Melius et al. | 604/385.31 |
| 6,811,642 B2 | * | 11/2004 | Ochi | 156/213 |
| 6,923,926 B2 | * | 8/2005 | Walter et al. | 264/119 |
| 2006/0021695 A1 | * | 2/2006 | Blessing et al. | 156/196 |

FOREIGN PATENT DOCUMENTS

EP 0 691 133 A 1/1996

* cited by examiner

*Primary Examiner* — Mark A Deuble
(74) *Attorney, Agent, or Firm* — William E. Gallagher; Richard L. Alexander

(57) ABSTRACT

An apparatus and an associated method comprise a receiving zone, for receiving solid material, a transferring zone, for transferring said solid material and optionally a releasing zone for releasing said solid material, e.g. to another moving surface and with a moving endless surface moving in and through said zones, said a moving endless surface has thereto a multitude of primary cavities and secondary cavities receiving said solid material, wherein said primary cavities are connectable and/or connected to said vacuum system of said transferring zone, and said secondary cavities are not connectable/connected to said vacuum system of said transferring zone, and wherein thus only said primary cavities transfer said solid material e.g. to said further moving surface; and wherein typically both primary and secondary cavities are connectable/connected to a vacuum system in said receiving zone.

20 Claims, 7 Drawing Sheets

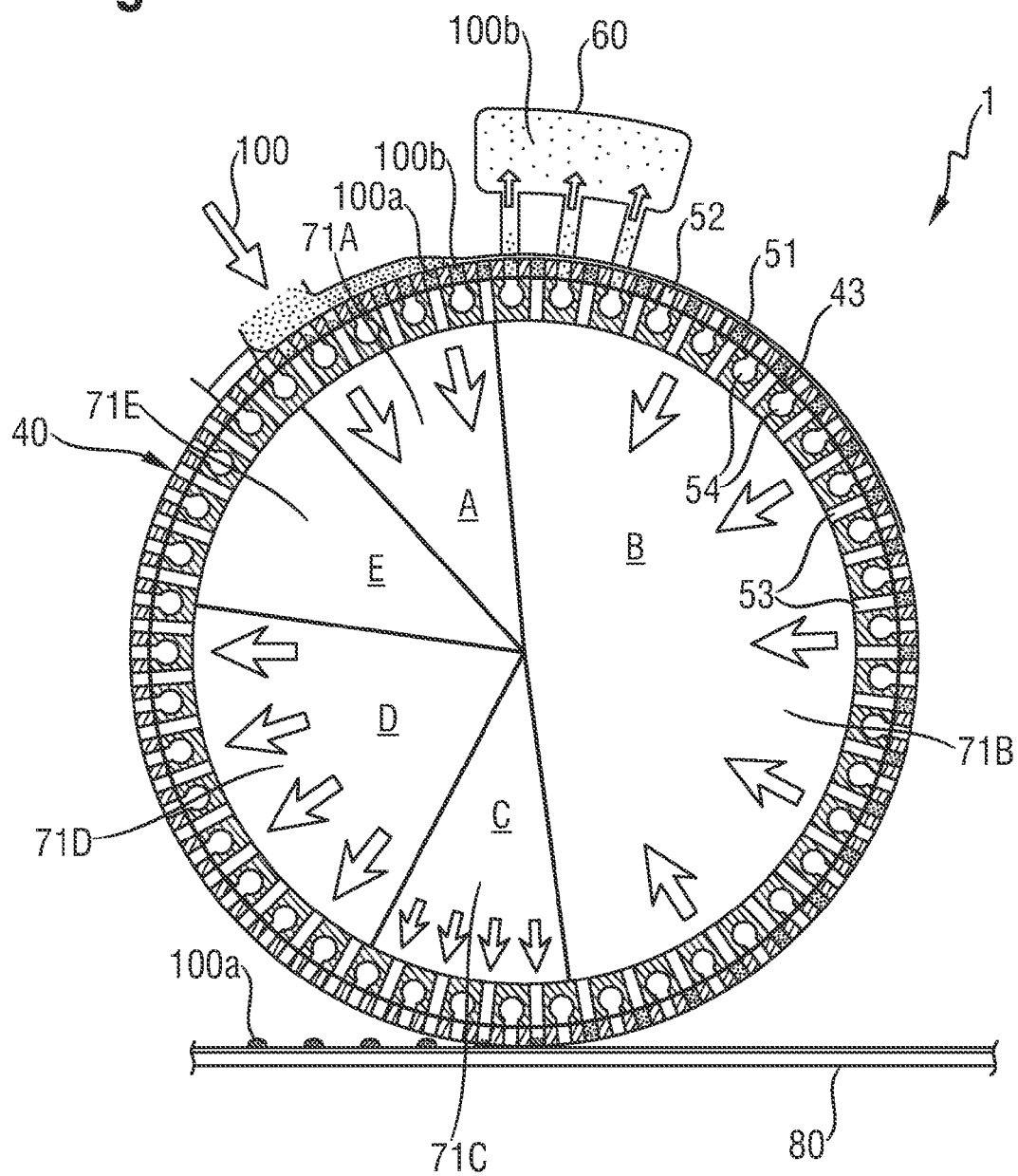

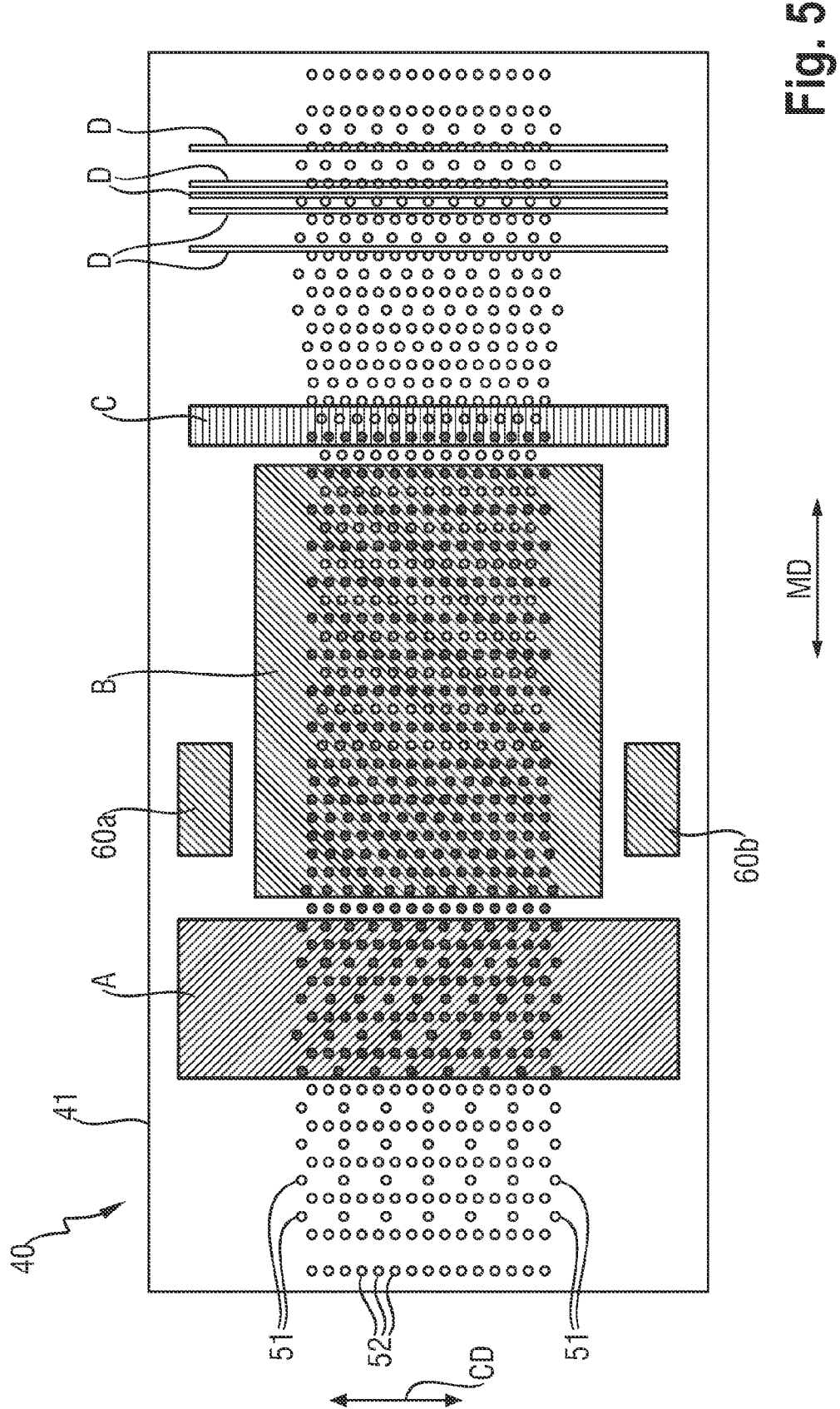

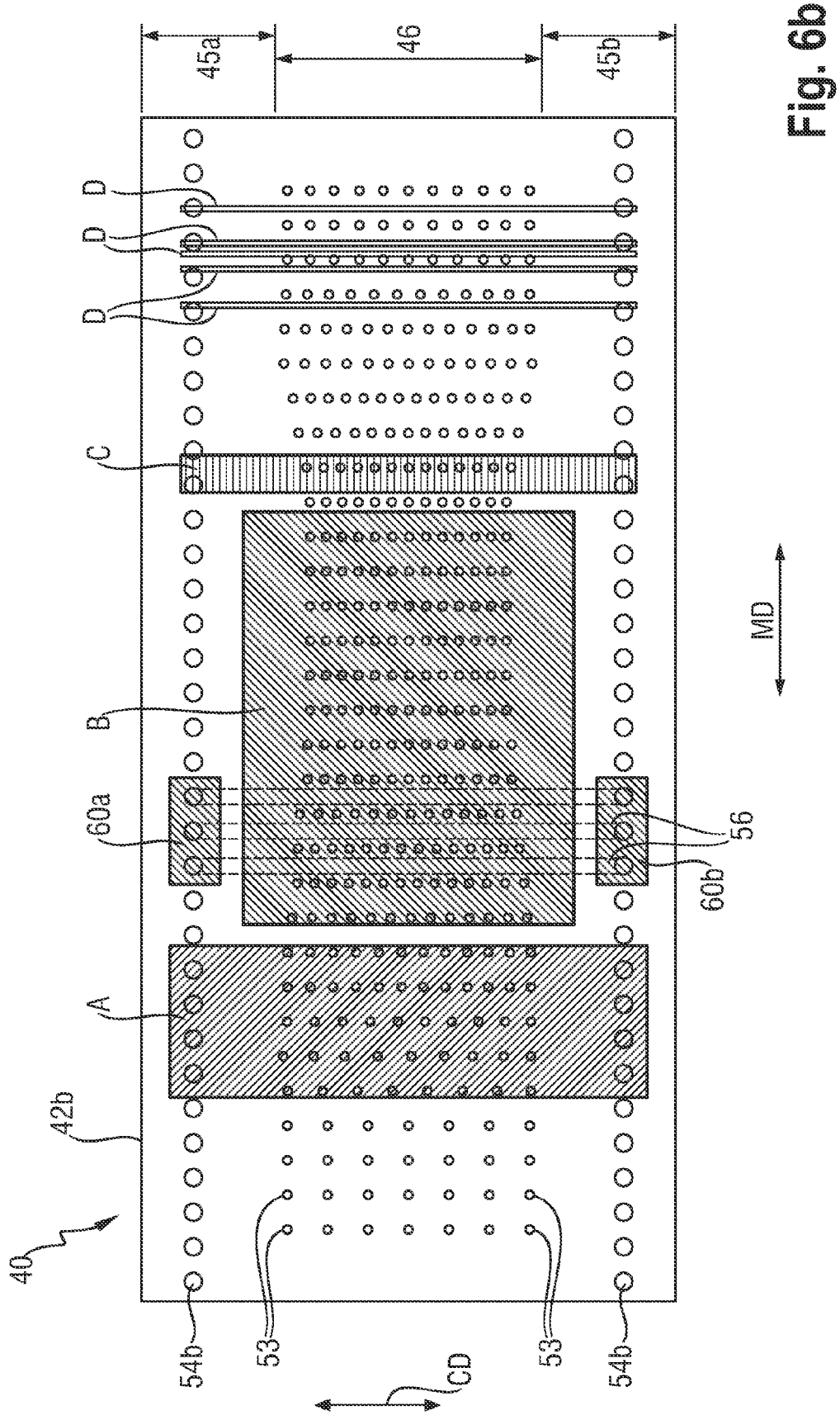

APPARATUS AND METHOD FOR RECEIVING AND TRANSFERRING SOLID MATERIAL

CROSS REFERENCE TO RELATED APPLICATION

This application claims priority to European Patent Application No. 10160396.7, filed Apr. 20, 2010, the substance of which is incorporated herein by reference.

BACKGROUND

The present application is directed to an apparatus with a receiving zone for receiving solid material; a transferring zone for transferring said solid material; and, optionally, a releasing zone for releasing the solid material, e.g. to a further moving surface, and with a moving endless surface moving in and through said zones, which has a multitude of primary cavities and secondary cavities receiving the solid material. The primary cavities are connected to a vacuum system in the transferring zone, and the secondary cavities are not connected to a vacuum system in said transferring zone. Thus, only the primary cavities transfer the solid material e.g. to the further moving surface. Thereby, both primary and secondary cavities typically are connectable/connected to a vacuum system in the receiving zone. The present application also relates to a method for receiving and transferring and releasing solid material, by use of the apparatus herein, or as described herein.

In the last decades, various processes have been proposed for making absorbent cores with fibers and/or superabsorbent polymer particles (SAP particles), also referred to as absorbent gelling polymer particles (AGM particles), including processes whereby said material is laid down on a moving surface, such as a drum surface, with one or more reservoirs and held onto said surface by vacuum. These approaches include indirect printing methods, whereby the AGM and/or fibers are taken up by a drum from one or more bulk storage(s) of said fibers and/or AGM particles, and whereby the drum then rotates towards a substrate such as a nonwoven, to then release the AGM and/or fibers onto the substrate. The drum may have one or more cavities, each being in the shape of a diaper core, that is then filled with fibers and/or AGM. However, such a complete diaper core shapes are difficult to transfer completely and accurately at high speed onto a second surface, such as a moving nonwoven web. In more recent years, it has been proposed to deposit fibers and/or AGM into smaller cavities. Such a multitude of smaller cavities may then together be in the form of a diaper core, so that when the AGM content of all the cavities is transferred onto a second surface, like a nonwoven web, a core is formed. This is for example described in EP-A-1621165. With such methods, a more accurate transfer of the solid material can be achieved, so that the resulting absorbent core may have a specific profile or distribution, such as a predetermined pattern,MD-, CD-, or thickness-profile, corresponding to the pattern/depth of the cavities.

Such proposed indirect printing processes are in some instances difficult to run at high speed, for example at speeds of more than 800 or more than 1000 parts (e.g. absorbent cores) per minute, and/or when fine particulate material is used, and/or when small (and large quantities of) cavities are used. Likewise, in such instances the solid material (such as fibers and/or AGM particles) are not always satisfactorily received by the cavities, resulting in inaccurate filling of the cavities, and hence insufficient transfer of the material and hence inconsistencies in the resulting absorbent cores.

Furthermore, when the process or apparatus is such that vacuum is needed to fill the cavities accurately, it is important that the vacuum/air flow through the cavities and/or solid materials is about constant, and/or that it is important that the vacuum/air flow per surface area is sufficient and about constant. When the process is very fast, and/or when the cavities are very small and/or when the particle material is of fine (particle) size, solid material may build up locally above the cavities, prior to flowing into the cavities, reducing the airflow (vacuum suction) in such areas. This may lead to inaccurate filling and insufficient transfer. For example, when the cavities are in the form of a pattern and thus have areas between the cavities, the vacuum/airflow may not always be sufficient or not sufficiently constant per surface area.

Furthermore, if the moving surface (such as a print roll or drum) comprises substantial zones (extending in machine direction, MD and cross-machine direction, CD) without cavities, for example corresponding to the zones between absorbent cores (of the web of absorbent cores produced by the method or with the apparatus) where for example the cores are to be separated from one another, continuous deposition of the solid material by the apparatus or process may result in build-up of said solid material. Even if a means is present to remove this build-up about immediately, such as a scraper blade, the air flow (vacuum) may already be impeded, and hence inaccurate filling of the cavities may occur.

SUMMARY

The present application generally relates to an apparatus and method to ensure continuous and accurate filling of cavities on a moving surface, resulting in a more consistent transfer, e.g. absorbent core formation, said method and apparatus being suitable even at high speeds and/or when small cavities are used for the transfer and/or even when fine particulate material is transferred.

The present application particularly relates to an apparatus having a receiving zone for receiving solid material, a transferring zone for transferring a first portion of said solid material and, optionally, a releasing zone for releasing said first portion of said solid material. The apparatus comprises:

- a moving endless surface, moving through the receiving zone, transferring zone and releasing zone of the apparatus, the moving endless surface comprising a multitude of primary cavities for receiving a first portion of the solid material, and a multitude of secondary cavities for receiving a second portion of the solid material;
- a vacuum system in the transferring zone for retention of the first portion of solid material during transfer, whereby the primary cavities are connectable to the vacuum system of the transferring zone, and the secondary cavities are not connectable to a vacuum system of the transferring zone, and;
- a removal means in the transferring zone for removing (in the transferring zone) the second portion of the solid material from the secondary cavities; and
- optionally, a releasing zone, where the first portion of the solid material is released from said primary cavities.

The primary cavities may be connectable to said vacuum system of the transferring zone. The primary cavities and/or, in some embodiments, the secondary cavities, may be connectable to a vacuum system of the receiving zone (and, thus, they are connected to the vacuum system when they move through the receiving zone).

The additional secondary cavities that are connectable to a vacuum system in the receiving zone may thus provide additional surface area for vacuum suction/air flow in the receiving zone, thus maximizing the vacuum suction/air flow through the moving endless surface in said receiving zone. This may aid stabilization of the vacuum suction/air flow in said receiving zone and may improve the solid material deposition in the primary and secondary cavities in the receiving zone.

The first portion of the solid material may be released from the primary cavities in a releasing zone, for example released onto a further moving endless surface such as, or comprising a substrate; this may be done by means of an gas-inlet system and application of (e.g. pressurized) gas through the primary (and optionally secondary) cavities, onto the solid material. The cavities may comprise a substrate material, e.g. web material, and the solid material is received thereon, and in the releasing zone, the solid material and substrate material is released from the moving endless surface.

The apparatus may have a vacuum chamber in the transferring zone, that may be connectable (and hence connected; indirectly connectable/connected, e.g., as described below, via e.g., at least the openings described below; or directly connectable/connected) to the primary cavities (but not to the secondary cavities); and optionally a vacuum chamber in the receiving zone that may be connectable/connected (indirectly connectable/connected, e.g. as described below, via e.g. at least the openings described below; or directly connectable/connected) to the primary cavities and optionally to the secondary cavities.

The moving endless surface may have an outer shell (41), that may comprise the primary and secondary cavities; and an inner shell comprising a multitude of primary openings and a multitude of secondary openings, and each of the primary cavities is connected to one or more primary opening, and via the openings connectable to the vacuum system (in the transferring zone and optionally in the receiving zone), and optionally a gas-inlet system in the releasing zone; and each of the secondary cavities is connected to one or more secondary opening, or a first part thereof, connectable (optionally via a second part of the secondary openings) to the removal means in the transferring zone, and optionally to the vacuum system in the receiving zone and optionally to a gas-inlet system in the releasing zone; optionally the moving endless surface comprising a screen positioned between the outer shell and the inner shell.

"Connected" or "connectable" as used herein includes directly and indirectly connected/connectable, unless stated explicitly otherwise.

"Multitude" as used herein with respect to the cavities, or openings, means at least 10, but in some embodiments at least 20 or at least 50.

The moving endless surface may contain at each moment in time at least: a part that is in the receiving zone, a part that is in the transferring zone and optionally a part that is in the releasing zone of the apparatus. Thus, for example, the primary cavities that are connectable to the vacuum system of the transferring zone, are connected to the vacuum system when moving through (and hence in) the transferring zone.

The present application also relates to a method for receiving with a moving endless surface solid material form a feeder, transferring the solid material with the moving endless surface and optionally releasing the solid material from the moving endless surface to a further moving surface, the method comprising:

(a) receiving a first portion of the solid material in primary cavities of the moving endless surface, and a second portion of the solid material in secondary cavities of the moving endless surface;

(b) optionally applying a vacuum during (a) onto the primary and secondary cavities;

(c) moving the moving endless surface to the further moving surface, while applying a vacuum to the primary cavities and the first portion of the solid material therein, and not to the secondary cavities and the second portion of solid material therein, thereby transferring the first portion of the solid material in the primary cavities, to the further moving surface, and not the second portion of the solid material;

(d) removing the second portion of the solid material from the secondary cavities with a removal means;

(e) optionally releasing the first portion of the solid material onto the further moving surface, e.g., by applying positive air pressure onto the primary cavities and the first portion of the solid material therein.

The present application further relates to a method for receiving with a moving endless surface solid material e.g., from a feeder, transferring the solid material (e.g. a first portion thereof) with the moving endless surface and releasing the solid material from the moving endless surface, e.g., to a further moving surface, using the apparatus described herein.

It should be understood that all aspect described with respect of the apparatus described herein are applicable to the method described herein or the method described herein for using such an apparatus, and that all steps to be performed by aspects or components of the apparatus described herein, are equally applicable to the methods described herein, and vice versa.

BRIEF DESCRIPTION OF THE DRAWINGS

Though the specification concludes with claims particularly pointing out and distinctly claiming the invention, it is believed that the present invention will be better understood from the following description taken in conjunction with the accompanying drawings, in which:

FIG. 4 is a schematic cross-sectional view through an illustrative apparatus of the present disclosure;

FIG. 5 is a schematic (partial) view of an illustrative outer shell of a moving endless surface at a moment in time;

FIG. 6*b* is a schematic (partial) view of an illustrative inner layer of the inner shell of a moving endless surface of FIG. 6*a* (at a moment in time).

DETAILED DESCRIPTION

Figure 1:
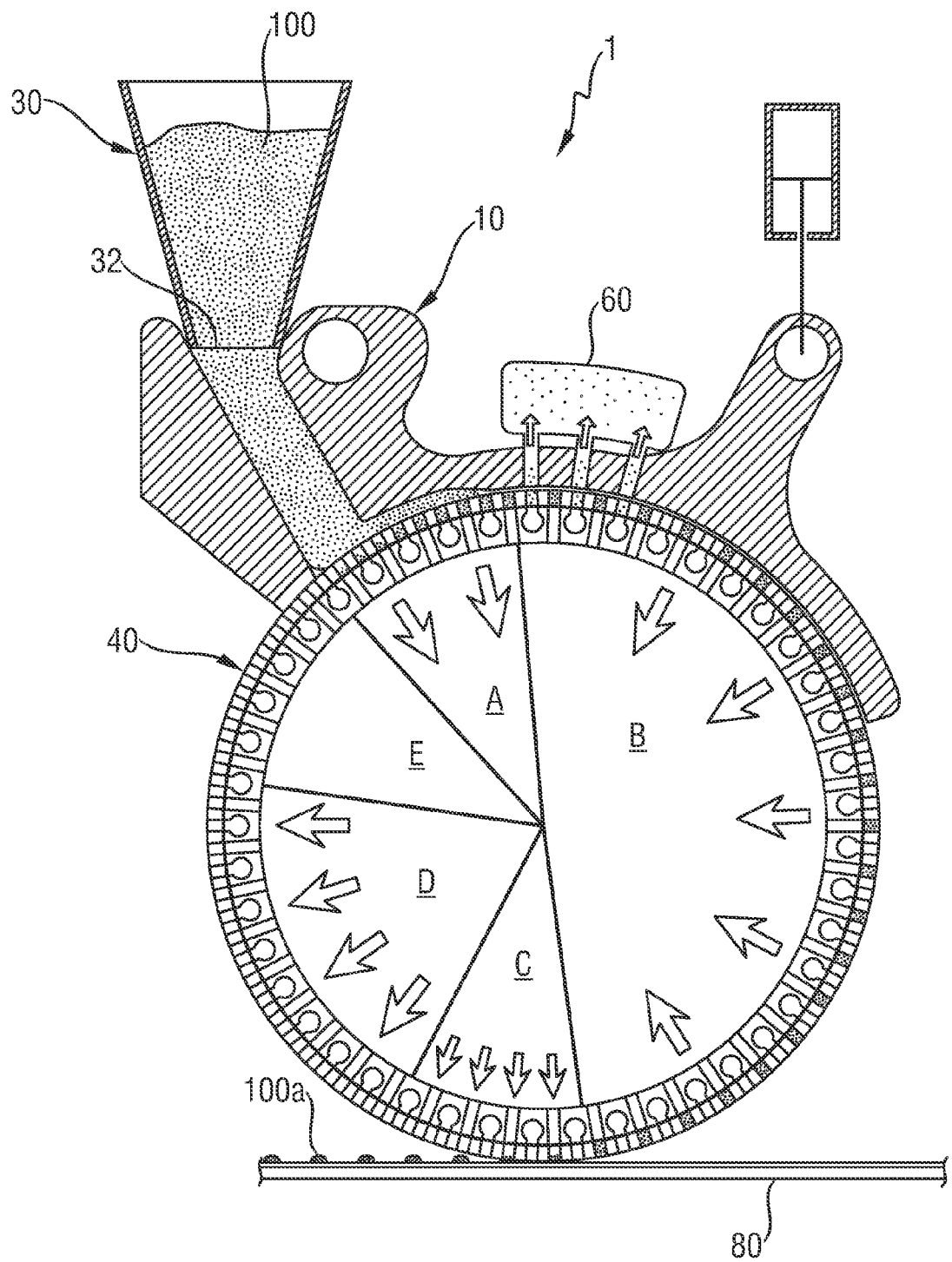
FIG. 1 is a schematic cross-sectional view through an illustrative apparatus of the present disclosure.
Figure 2:
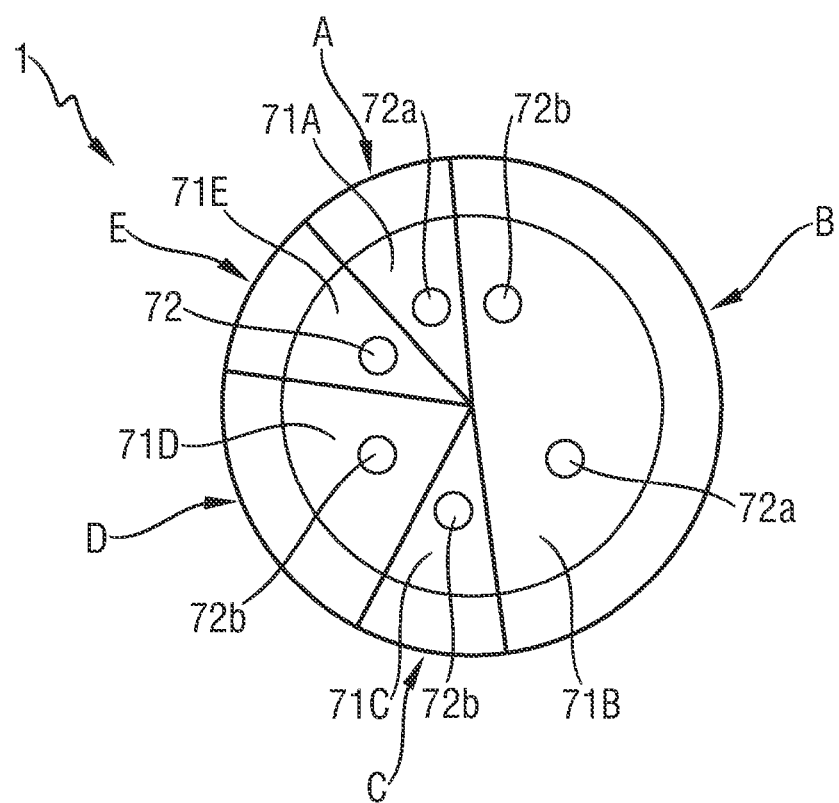
FIG. 2 is a schematic cross-sectional view through an illustrative apparatus of the present disclosure, and its vacuum systems(s) and gas-inlet systems(s)

The solid material 100 herein may be any material that is processable in the method and apparatus described herein, e.g., flowable; generally, the solid material is in particulate form, which includes particles, including granules, spheres, agglomerated particles; flakes; fibers; and other forms known in the art; and mixtures thereof. The solid material may be a mixture of fibers and particles.

In one or more embodiments herein, the solid material may include or consist of fibers, such as cellulose or cellulose-based fibers, including modified cellulose fibers. In one or more embodiments herein, the solid material 100 comprises or consists of particles, such as detergent particles, medical ingredient particles, etc. In one or more embodiments herein, the solid material 100 comprises or consists of absorbent or superabsorbent material in the form of particles, e.g., (super) absorbent polymeric material in the form of particles, also known as particulate absorbent gelling material, herein referred to as AGM. This typically refers to polymeric materials in particulate form that can absorb at least 10 times their weight of a 0.9% saline solution, i.e., having a CRC value of at least 10 g/g as measured using the Centrifuge Retention Capacity test of EDANA (European Disposables and Non-wovens Association), test method No. 441.2-02 "Centrifuge retention capacity". The particulate AGM herein may have a higher sorption capacity, e.g. having a CRC of for example at least 20 g/g, or at least 30 g/g.

The particulate AGM may have a good permeability for liquid, for example, having a SFC value of at least $10 \times 10^{-7}$ $cm^3 \cdot s/g$; or at least $30 \times 10^{-7}$ $cm^3 \cdot s/g$, or at least $50 \times 10^{-7}$ $cm^3 \cdot s/g$, $10 \times 10^{-7}$ $cm^3 \cdot s/g$, or possibly permeability SFC value of at least $100 \times 10^{-7}$ $cm^3 \cdot s/g$, or at least a SFC of $120 \times 10^{-7}$ $cm^3 \cdot s/g$. This SFC is a measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution). Upper limits may be, for example, up to $350 \times 10^{-7}$ $cm^3 \cdot s/g$ or up to $250 \times 10^{-7}$ $cm^3 \cdot s/g$.

In one embodiment herein the polymers of the AGM are internally cross-linked and/or surface crosslinked polymers. In one embodiment herein, the polymers are polyacrylic acids/polyacrylates, for example having a neutralization degree of from 60% to 90%, or about 75%, having for example sodium counter ions, as known in the art, e.g. surface crosslinked and/or internally crosslinked polyacrylic acid/polyacrylate polymers.

In one embodiment herein, the solid material 100 has, or is in the form of particles with, a mass medium particle size up to 2 mm, or even between 50 μm and 2 mm or to 1 mm, or from 100 μm or 200 μm or 300 μm or 400 μm, to 1000 μm or 800 μm or 700 μm; as can for example be measured by the method set out in for example EP-A-0691133. In one embodiment herein, the solid material 100 is in the form of particles with particle sizes between 50 μm or 100 μm, and 1200 μm or 1000 μm. In yet other or additional embodiments, the particulate material 100 has a relatively narrow range of particle sizes, e.g., with the majority (e.g. at least 80% or at least 90% or even at least 95%) of particles having a particle size between 50 μm and 1000 μm, or between 100 μm and 800 μm, and or between 200 μm and 600 μm.

The solid material 100 herein may advantageously comprise less than 15% by weight of water, or less than 10%, or less than 8% or less than 5%. The water-content can be determined by the Edana test, number ERT 430.1-99 (February 1999) which involves drying the solid material 100 at 105° C. for 3 hours and determining the moisture content by the weight loss of the solid material 100 after drying.

The particulate AGM herein may be particles of AGM that are surface coated or surface treated (this not including surface-crosslinking, which may be an additional surface-treatment); such coatings and surface treatment steps are well known in the art, and include surface treatment with dusting agents such as inorganic powders, including silicates, phosphates, and/or coloring agents, and/or pigments; and/or a coating of polymeric material, including elastomeric polymeric materials, or film-forming polymeric materials; hydrophilic coating agents, including cationic compounds; and combination thereof. The apparatus 1 herein has a receiving zone A for receiving solid material, a transferring zone B, for transferring a first part of the solid material and optionally a releasing zone C for releasing a first part of the solid material 100 *a*. The zones may be defined by the function they have, e.g., receiving of solid material in the receiving zone, e.g. from one or more sources such as a feeder, e.g. a hopper; transfer in the transferring zone B of solid material, from the receiving zone A, where the material is received by the surface 40; it may be transferred to any further processing step, for example it may be transferred to a zone of the apparatus where it is released from the surface 40, in the releasing zone C, (e.g., released to a further moving endless surface 80, for example a substrate as described hereinafter). The method herein has corresponding method steps. The moving endless surface 40 of the apparatus 1 moves through the zones. At each point in time, the moving endless surface 40 thus also has a receiving zone A, transferring zone B and optionally a releasing zone C (but this various over time, due to movement of the surface). In some embodiments herein, the apparatus 1 has stationary components, adjacent the moving endless surface 40 and the stationary component define the zones, e.g. the apparatus has a stationary receiving zone component, e.g. vacuum system of chamber 71A, a stationary transfer zone B component, e.g., a vacuum system or chamber 71B and releasing means 60; and a stationary releasing zone component, e.g., gas-inlet system 72 *b*. In one or more embodiments herein, the receiving zone A has a feeder 30 and the vacuum system/chamber, the transferring zone B has a the vacuum chamber/system and a removal means 60 for removing solid material including for example one or more gas (air)-inlet systems or chambers, and the optional releasing zone C may have a gas (air) inlet system or chamber. The moving endless surface 40 moves for example (e.g. rotates) in and through the zones, adjacent the system/chambers and removal means 60.

The solid material is received by a moving endless surface 40 in the primary and secondary cavities 52 thereof, described below; a first portion of the solid material 100a is received by the primary cavities 51 and a second portion of the solid material 100b is received by the secondary cavities 52. The cavities may comprise a substrate material, for example a web material, and the solid material may be received thereon in the receiving zone, and this substrate material may be released, e.g., together with the solid material, in the releasing zone C. For example, the cavities may comprise an (e.g., air-permeable) film material, that will form a coating or cover for the solid material, e.g., to form tablets or capsules or pouches or the like.

In one or more embodiments herein, the cavities do not comprise a substrate material that is released/releasable from the cavities, and the solid material is thus directly received into the cavities.

The solid material 100 may be received from one or more feeders, e.g., present in the receiving zone adjacent the surface. The solid material 100 leaves the feeder 30 and contacts the moving endless surface 40 in the receiving zone. The feeder(s) 30 herein may thus be any feeder, capable of holding the solid material 100, typically in bulk quantities, and capable of letting it flow to the moving endless surface 40.

The feeder 30 may have a container portion, to hold the solid material 100, e.g., having a volume of at least 1000 cm³, and a guiding portion, e.g., a pipe-shaped portion that guides the solid material 100 from the container portion to the moving endless surface 40. In one embodiment it has a funnel shape, as shown, for example, in FIG. 1, having a container portion and a pipe-shaped portion. The feeder 30 has for example an opening 32 having opening edges positioned adjacent the moving endless surface 40, and typically in proximity thereto; hereby the distance from the opening edges to the first moving endless surface 40 may be for example less than 10 cm, or less than 5 cm, and it may for example be less than 2 cm or less than 1 cm, and for example at least 0.1 mm, or at least 1 mm. The opening 32 may have any form, including circular or oval; in one embodiment, the opening 32 is rectangular.

Figure 4A:
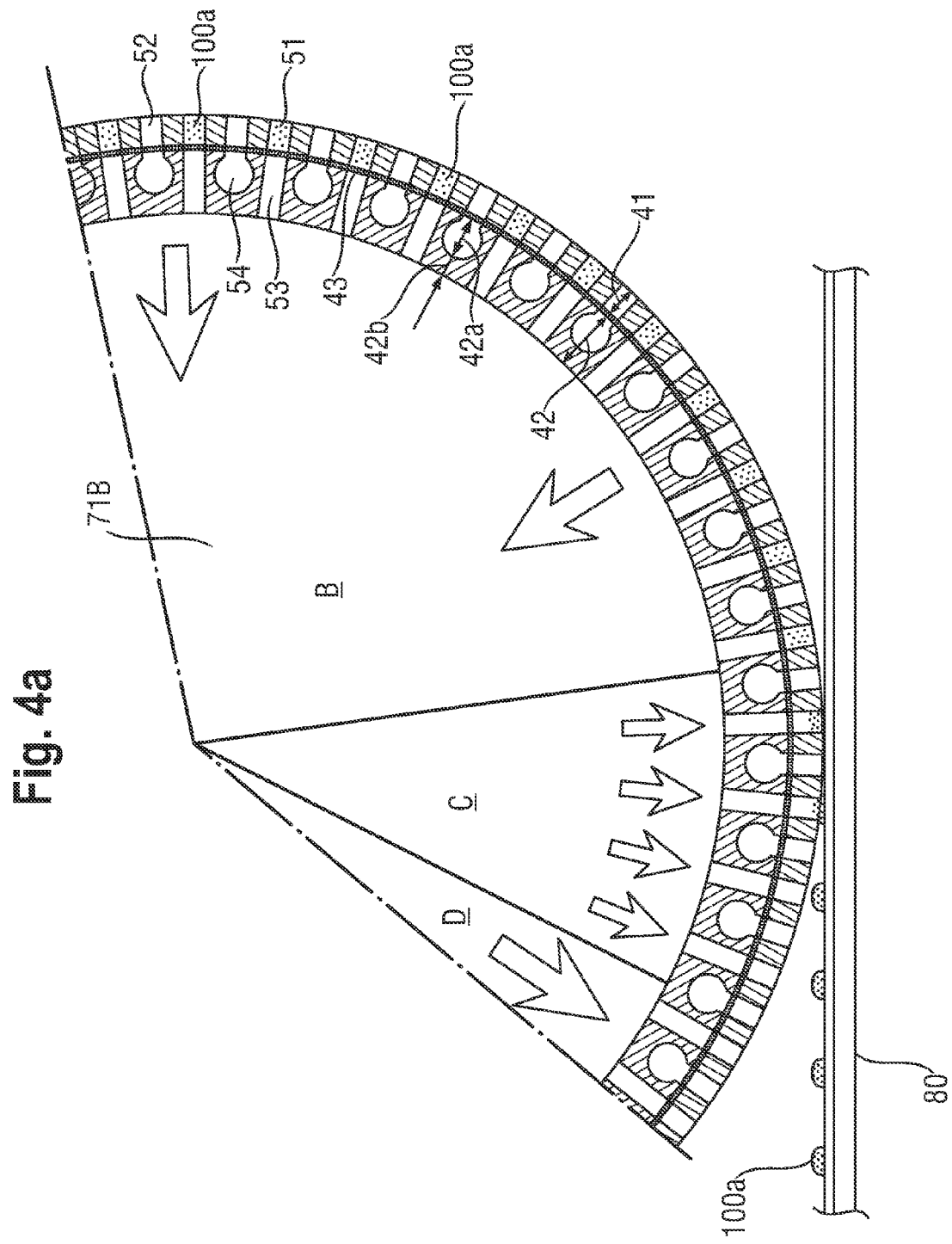
FIG. 4*a* is an enlarged view of a section of the schematic cross-sectional view through an illustrative apparatus of FIG. 4.

In one embodiment, the feeder 30 is positioned above the moving endless surface 40, for allowing gravity to help to "feed" the solid material 100 to the moving endless surface 40. Hereto, (an opening edge of) the feeder 30 may be positioned exactly above the moving endless surface 40 (0°), or, when the moving endless surface 40 is curved, or even for example circular, as shown in the FIGS. 1 and 4, it may be positioned substantially above the surface, which means at any position between 90° and −90° (e.g. between 9 o'clock and 3 o'clock position), or in one embodiment between 60° and −60°, or between 30° and −30° (measured as angle between an distal edge of the opening 32 and the force line of gravity).

The moving endless surface 40 herein may be any moving endless surface, for example a moving surface that can rotate to provide a moving endless surface. It may, for example, be a transporter belt, or the movable (e.g. outer) surface of a cylinder or drum or roll, as known in the art, which can rotate and thus provide a moving endless surface 40. The moving endless surface with cavities may be covered or partially covered (e.g. overlaid or partially overlaid) or by a further substrate material, e.g., that may line the primary cavities or the primary and secondary cavities, so that thus the solid material is received onto the substrate material. Hereto, the substrate material is then air permeable, but substantially non-permeable for the solid material.

The moving endless surface 40 has a direction of movement (e.g. rotation), herein referred to as MD. The moving endless surface 40 may be a rotating surface with a certain radius. The radius of the moving endless surface 40 may depend on what structure is produced, and what size of structure is produced, and for example how many structures are produced per cycle of the moving endless surface 40, e.g., drum. For example, the surface and/or drum may have a radius of at least 40 mm, or of at least 50 mm; it may be for example up to 300 mm, or up to 200 mm.

The first moving endless surface 40 may have any suitable width; for example it may have a width (perpendicular to MD) corresponding (substantially) to the width of the structure to be produced; in some embodiment herein the surface has a central zone 46, extending in MD, that corresponds substantially to the width of the structure to be produced, and it has one or two lateral edge zone(s) 45a, 45b, extending in MD, on one or both sides of the central zone 46, that for example not comprise primary cavities 51, or not comprise primary and secondary cavities 52, as described below.

The width of the moving endless surface 40 or central zone 46 thereof, may for example be at least 40 mm, or at least 60 mm, or for example up to 600 mm, or up to 400 mm. If present, the lateral edge zone or zones may for example be between 5 mm and 200 mm, or to 100 mm or to 70 mm The moving endless surface 40 comprises primary cavities 51 and secondary cavities 52; e.g. protruding through part of the surface (in Z-direction), to have a certain depth to receive the solid material; in other words, the primary and secondary cavities 52 have a void volume that can be filled with solid material 100. A first portion of the solid material is received by the primary cavities 51 and a second portion of the solid material is received by the secondary cavities 52.

In some embodiments, described in more detail below, the moving endless surface 40 has a shell 41 that comprises the primary and/or secondary cavities 52 and an inner shell 42, not comprising the cavities, but comprising for example the primary and secondary openings 53,54 herein described below.

The surface area between the primary 51 and secondary cavities 52, thus not comprising cavities, is herein referred to as "outer surface area" of the moving endless surface 40. The remaining surface area formed by the cavities is the open surface area of the moving endless surface 40 composed of the total open surface area of the primary cavities 51 and total open surface area of the secondary cavities 52.

Thus, each primary cavity and each secondary cavity has an open surface area, with is the open surface area of a cavity (measured) in the plane of the "outer surface area" of the moving endless surface 40; the ratio of the total open area of all primary cavities 51 to the total open area of all secondary cavities 52 may be for example from 50:1 to 1:10, or for example from 30:1 or 20:1 or 10:1 or 5:1 to 1:10 or to 1:5 or 1:3 or to 1:2, or even about 1:1.

The exact cavity dimensions and/or pattern will depend on the required structure to be formed; it may for example (also) depend on the particle size of the solid material 100, the process speed etc. In some embodiments at least 5% or at least 10% or at least 20%, or in some embodiments, at least 30%, or at least 35%, of the moving endless surface 40 or, in some embodiments, of the central zone 46 thereof, is open area, i.e. comprises the primary 51 and secondary cavities 52; the maximum open area of the moving endless surface 40 or the central zone 46 thereof may for example be 70% or less or 60% or less (the central zone being described below).

Alternatively, or in addition, each primary cavity may have a certain maximum depth, which is at least 1 mm (as described below) and each secondary cavities 52 may have a certain maximum depth, being at least 1 mm, and the total volume of all the primary cavities 51 to the total volume of all the secondary cavities 52 is for example from 50:1 to 1:10, or for example from 30:1 or 20:1 or 10:1 or 5:1 to 1:10 or to 1:5 or 1:3 or to 1:2, or even about 1:1.

The primary and secondary cavities 51, 52 may have any shape, including cubical, rectangular, cylindrical, semi-spherical, conical, or any other shape. In some embodiments herein, the primary and/or secondary cavities are cylindrical. The primary cavities 51 or secondary cavities 52, or both, may be present as identical cavities, or they may vary in dimension(s) or shape.

The primary cavities 51 and/or secondary cavities 52 may have any dimension; in general, each cavity has a maximum depth (in Z-direction; measured from the outer surface of the moving endless surface to the lowest point on the surface that receives the solid material) of at least 1 mm, or for example at least 1.5 mm or at least 2 mm, for example up to 20 mm, or up to 15 mm, or in some embodiment herein, up to 10 mm, or to 5 mm or to 4 mm. Each primary and secondary cavity has a base surface area, which may for example be flat, or curved, or conical shaped, upon which the solid material is deposited, and that comprises the maximum depth point. The depth of the cavities may be uniform per cavity and then the maximum depth equals the depth of the cavity as a whole. In some embodiments, this base surface area of the cavities is substantially flat.

The base surface may for example be partially open to allow gas transfer but not solid material transfer. In some embodiments, the base surface area of the cavities may be open, but adjacent (e.g. overlaid/superposed by) a screen 43 described hereinafter, onto which the solid material is received; such a screen may be is gas-permeable but substantially non-permeable for solid material, as for example shown in FIG. 4a.

Each primary cavity 51 may have the same (max.) depth; each secondary cavity 52 may have the same (max.) depth; the primary and secondary cavities 51, 52 may have the same (max.) depth. In some embodiments, the primary cavities 51 have a maximum depth that is greater than the maximum depth of the secondary cavities 52.

The distance in MD between the center point of a primary cavity or of a secondary cavity (the center point being in the plane of the outer surface of the moving endless surface 40) and the center point of a neighboring closest cavity (which may a primary or secondary cavity) may for example be 1 mm or more, or 2 mm or more, and/or for example up to 20 mm or up to 15 mm or up to 10 mm (e.g., between cavities in a line of cavities, extending in MD). This may apply to all such distances between neighboring cavities in MD, or this may be an average over all such distances.

The distance in CD between the center point of a primary or secondary cavity (the center point being in the plane of the outer surface of the moving endless surface 40) and the center point of a neighboring closest cavity (primary or secondary) may for example be 1 mm or more, or 2 mm or more, and/or for example up to 20 mm or up to 15 mm or up to 10 mm; (in a row of primary cavities 51, this distance is thus between neighboring primary cavities 51); and in a row of secondary cavities, this is between neighboring secondary cavities 52.

These CD and MD distances may vary over the surface or may be uniform. Furthermore, the CD distance between primary cavities 51 of a row of primary cavities may be different to the CD distance between secondary cavities 52 of a row of secondary cavities.

In one embodiment, the MD dimension of a primary cavity may be measured (on average over all primary cavities and/or for each primary cavity) over the outer surface of the moving endless surface 40) at least 1 mm, or at least 2 mm, or at least 4 mm, and for example at the most 20 mm or at the most 15 mm; and equally for the secondary cavities 52.

The CD dimension may be within the same ranges as above, or it may even be the same as the MD dimensions for one or more or each cavity. In some embodiments herein, the primary and/or secondary cavities 52 are cylindrical and the MD/CD dimension is then the diameter of the cavities.

The secondary cavities 52 or part thereof may be in the form of channels, extending in CD. Then, the CD-dimension is significantly more (e.g. at least 2 times, or at least 4 times) than the MD dimension of the channel.

According to some embodiments herein, the primary and/or secondary cavities are cylindrical, each having a diameter (MD/CD dimension) of from 2 mm to 8 mm or from 3 mm to 7 mm; and the primary and/or secondary cavities may have a maximum depth and/or average maximum depth of for example from 1.5 mm to 4 mm, or to 3 mm.

The primary 51 and/or secondary cavities 52 may be present as a pattern, for example of a multitude (e.g. 3 or more) of rows of a two or more, for example 3 or more or 4 or more, primary cavities 51 and a multitude (e.g. 3 or more) of rows of one or more (e.g. 3 or more, or 4 or more) secondary cavities ("row" when used herein being a row extending in CD). For example, the moving surface may have a multitude of CD-extending channel-shaped cavities, and/or, n some embodiments, a multitude of rows of a multitude of cavities, e.g. conical or cylindrical-shaped cavities.

For example, at least 10 or at least 15 rows of primary cavities 51 may be present and/or at least 10 or at least 15 or at least 20 CD-extending rows of secondary cavity (s) may be present.

The primary cavities 51 and secondary cavities 52 or part thereof, may be present as a one or more, generally at least 3 or at least 4 lines (in MD) formed by a primary and secondary cavities. For example, at least 3 or at least 4 or at least 5 MD-extending lines of primary cavities 51 and/or lines of secondary cavities 52 may be present on the surface.

The moving endless surface 40 may comprise a pattern of alternating rows, i.e. a row of primary cavities 51 followed by a row of secondary cavities 52, etc. In some embodiments herein, at least 30% or at least 50% or at least 60% of the rows of the primary cavities 51 and of the rows of the secondary cavities 52 are alternating primary cavities row and secondary cavities rows.

The alternating pattern may be the pattern over the whole moving endless surface 40, or the central zone 46 thereof, or over only a part thereof, or only over a part of the central zone 46. For example, the moving endless surface 40 may have one or more areas comprising a multitude of rows of secondary cavities 52, but not comprising any primary cavities 51 ("secondary cavities row zones"). This may correspond to the areas of the resulting web of structures produced by the apparatus (1) and method herein that is to be cut to separate the web into individual structures. For example, in some embodiment herein, the apparatus (1) and method herein serves to produce a series of articles, e.g. absorbent cores that are not continuous. Then, the areas where no primary cavities 51 are present correspond to the areas between produced articles, to form the discontinuity between two articles. For example, when absorbent cores are produced with the method or apparatus (1) herein, comprising the solid absorbent material transferred and released to a substrate, e.g. nonwoven, then these areas may correspond to the areas of the nonwoven between absorbent structures (cores), where the nonwoven may be cut, to form individual structures (cores). This is for example shown in FIGS. 5, 6a and 6b.

In some embodiments, at least 10% or at least 20%, but for example up to 40% or up to 30% of the rows of secondary cavities are not alternating, e.g. for example those present in the "secondary cavities row zones."

The primary cavities 51 are connected/connectable to a vacuum system 71B of the transferring zone B. The secondary cavities 52 are not connected/connectable to a vacuum system 71B in the transferring zone B.

The secondary cavities 52 are connected and/or connectable to a solid material removal means 60 of the transferring zone B; this may comprise a gas (e.g. air)-inlet system, that allows a gas (air) to enter through the secondary cavities 52, to blow the second portion of the solid material 100b from the secondary cavities 52, to remove it from the moving endless surface 40, as shown in FIGS. 1 and 4. The removal means 60 may comprise a collecting vessel to collect the solid material 100b thus removed, e.g., blown from the secondary cavities 52, as for example shown in FIG. 1.

In some embodiments, no vacuum (system) is present or applied, e.g. no vacuum chamber is present, in the releasing zone C. In the releasing zone C, it may be useful to apply positive gas (air) pressure, e.g. by means of introducing/blowing a gas (air), onto the solid material, via the cavities, or part thereof. Thus, in some embodiments herein, the releasing zone C, if present, comprises a gas-inlet system/gas (air) chamber, connectable to the primary cavities, to enable or improve release of the first portion of the solid material 100*a* from the primary cavities 51, for example onto a further moving surface (substrate). The secondary cavities may also be connected to a the gas inlet system, to further remove solid material of the secondary cavities 52.

The primary and secondary cavities have each a base surface area to receive the solid material on; this may be partially open, allowing gas transfer (permeability), for vacuum suction/air inlet, but not solid material transfer (permeability) there through; in some embodiment herein the base surface areas of the primary and secondary cavities may be substantially or completely open, but superposed and/or overlaid by the screen 43, (that allows gas transfer but not solid material transfer; e.g. a mesh screen), and thus substantially closed by the screen 43. In some embodiments the cavities may comprise a substrate material, e.g. web material, and the solid material is received thereon, and in the releasing zone, the solid material and substrate material is released from the moving endless surface.

The vacuum may be provided by any known vacuum system, connectable to a moving surface. The vacuum system 71B,71A typically comprises a stationary component. In some embodiment, the method and/or apparatus 1 involves a cylindrical drum or roll, with the rotating, cylindrical moving endless surface 40 and enclosed therein one or more vacuum chambers 71A, 71B. The chambers 71A and 71B may be a single unitary chamber, but in some embodiment herein, they are separate chambers. In some embodiment, the transferring zone B has a first vacuum chamber B and the receiving zone a second vacuum chamber A, e.g. so that different vacuum levels can be applied in the different zones. Each chamber has typically an inlet, for connection to an external (e.g. not adjacent the moving surface, and/or not inside the drum) vacuum source, for vacuum suction.

In some embodiments herein, the primary and secondary cavities 52 are connectable and/or connected to a vacuum system 71A of the receiving zone. Hereto, the apparatus 1 or method may employ a vacuum chamber adjacent the moving surface in the transferring zone B, chamber 71B, for example positioned adjacent the central zone 46, and in the receiving zone, chamber 71A, for example positioned under the central zone and optionally under the lateral edge zones) 45 *a*, 45*b*; the apparatus 1 or method may employ an gas-inlet system in the transferring zone B, e.g. being part of the removal means 60, and/or the releasing zone C, e.g. a gas-inlet chamber C, for example positioned adjacent the edge zone(s) 45*a*, 45*b*. The vacuum may be of any vacuum pressure such as for example at least 10 kPa, or at least 20 kPa.

In some embodiments, the vacuum applied in the receiving zone is different to, for example less than, the vacuum applied in the transferring zone B.

Figure 6A:
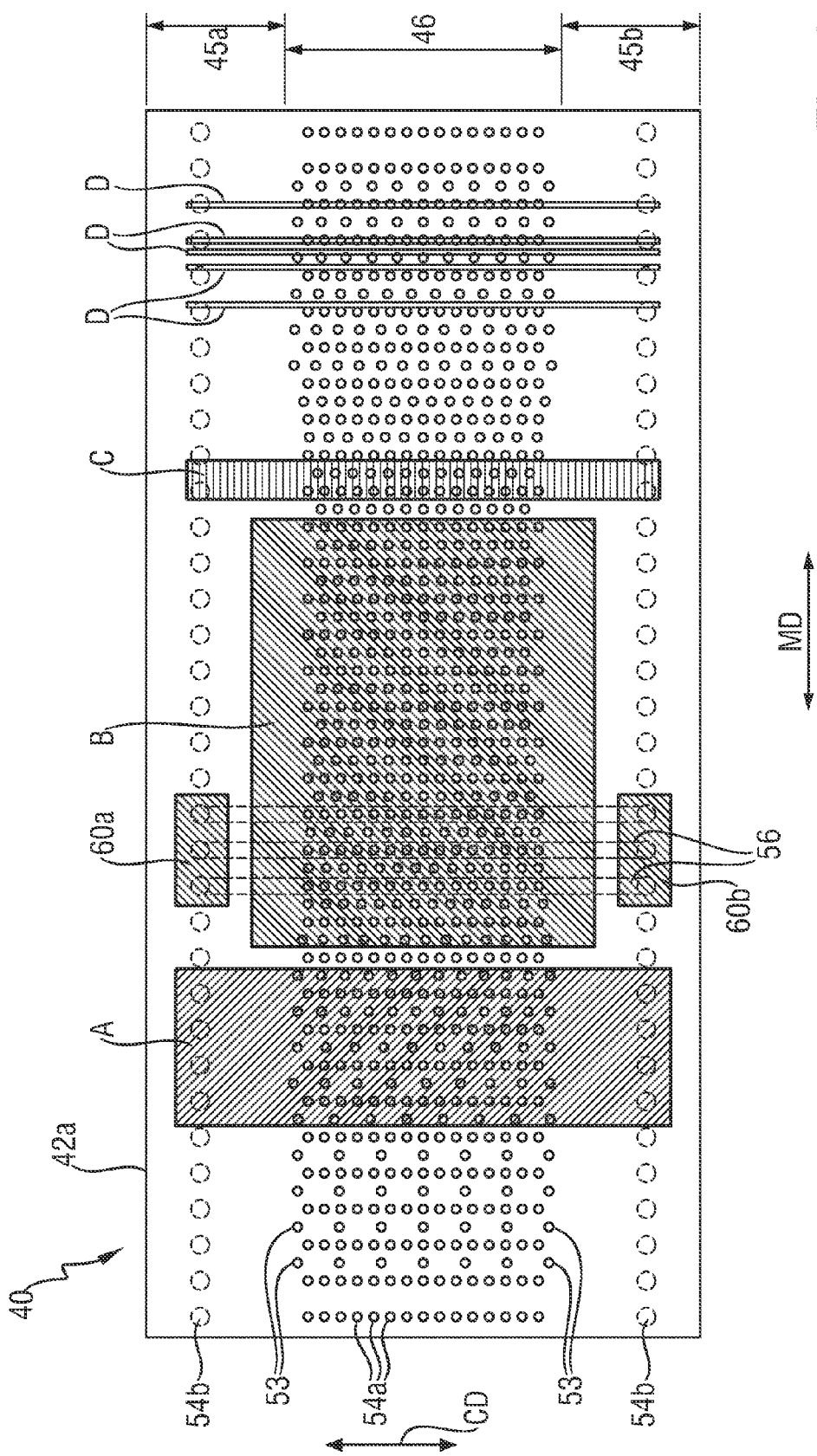
FIG. 6*a* is a schematic (partial) view of an illustrative inner shell of a moving endless surface at a moment in time, showing its outer layer thereof; this may be used in combination with the exemplary outer shell of FIG. 5.

As shown for example in FIGS. 5, 6, and 6A, each of the primary cavities 51 may be connectable and/or connected to the vacuum system 71B, or optionally 71A via primary openings 53 in the moving surface, for example present in the inner shell 42 of the moving surface, so that thus the primary openings form the connection between the primary cavities 51 and the vacuum system 71B; optionally 71A. Hereto, the moving surface may have for example an outer shell 41 comprising the primary cavities 51 and an inner shell 42 comprising the primary openings. In some embodiments, the primary openings are through-openings, through the inner shell 42 of the moving surface; however, alternative connections of the cavities to the vacuum system 71B by use of the openings are envisaged herein. In some embodiment, the secondary cavities 52 may be connectable and/or connected to the vacuum system 71A of the receiving zone (but not in the transferring zone B), and/or connectable/connected to a gas-inlet system 60; 72*b* of the transferring zone B, via secondary openings 54 *a*, 54*b* in the moving surface, e.g. in the inner shell 42 thereof, that form the connection between the secondary cavities 52 and a vacuum system 71B/gas-inlet system 60; 72*b*. Hereto, the moving surface may have an outer shell 41 comprising the secondary cavities 52 and an inner shell 42 comprising the secondary openings 54 *a*, 54*b*. Thus, the base surface area of each of the cavities may thereto be connected to the top surface area of an opening.

Some or all of the primary cavities 51 may be connected and/or connectable to the vacuum system 71B; optionally 71A or gas-inlet system by connecting each primary cavity to a single primary opening, or alternatively 2 or more, or a multitude, of primary cavities 51 are connected to a shared primary opening. Alternatively, or in addition, some or all of the secondary cavities 52 may be connectable and/or connected to the vacuum system 71A of the receiving zone A by connecting each secondary cavity to a single secondary opening, or alternatively 2 or more, or a multitude of, secondary cavities 52 are connected to a shared secondary opening.

The primary openings 53 and secondary openings 54, or first part thereof 54*a* may for example have shape/dimensions/open area (ratios)/positioning (e.g. rows) as described above for the primary and/or secondary cavities; the primary cavities may for example have the same dimensions/positioning/shape as the primary openings; and/or the secondary cavities may have the same dimensions as the secondary openings, or first part thereof.

As mentioned above, a screen 43 may be placed adjacent the cavities, for example between the inner shell 42 and outer shell 41, so that the screen is present between the cavities and the openings. The screen may be a material, that allows a gas to pass, but substantially no solid material, for example a mesh screen with a mesh opening size of less than 100 µm, or less than 50 µm or less than 20 µm, or less than 10 µm. In some embodiments, the base surface of some or all of the primary cavities 51 is formed by the screen. In some embodiment, the top surface of some or all of the primary openings is formed by that screen.

In some embodiments, and as for example shown in FIGS. 1, 4, 4*a*, 5, 6*a*, and 6*b*, the moving surface 40 has an outer shell 41, comprising the primary and secondary cavities and an inner shell 42 comprising a multitude of primary openings 53 and a multitude of secondary openings 54 *a*, b, and each of the primary cavities 51 is connected to a (e.g. different) primary opening 53, and via the openings connectable to the vacuum system 71B; and each of the secondary cavities 52 is connected to a (e.g. different) secondary opening, or for example to a first part of the secondary openings 54 *a*, connectable (optionally via a second part 54*b* of the secondary openings 54 *a*, 54*b*, see below) to: a vacuum system 71A (e.g. when moving through or in the receiving zone); and/or to gas (air) inlet system (e.g. when moving through or in the transferring zone B); the moving surface for example comprising a screen 43 positioned between the outer shell 41 and the inner shell 42.

As shown in FIGS. 4, 4*a*, FIGS. 6*a* and 6*b*, for example, the inner shell 42 may have a first outer layer 42*a* and a second inner layer 42*b*. In some embodiments herein, the moving endless surface 40 is a rotating cylindrical drum (or roll), having thus a rotating cylindrical inner shell 42 and rotating cylindrical outer shell 41, that are connected and typically joined to one another.

The first part of the secondary openings 54a, or all the secondary openings (and the primary openings) may be present in the first outer layer 42a of the inner shell 42, but whereby the first part of the secondary openings are not present in the second inner layer 42b of the inner shell 42, while the second part of the secondary openings and the primary openings are present in the second inner layer 42b of the inner shell 42, to be connectable to the vacuum and/or gas-inlet system. In some embodiments herein, and as shown in FIGS. 4, 4a, FIGS. 6a and 6b, for example, the first part of the secondary openings 54a or all of the secondary openings 54 a, 54b is (are) present in the first outer layer 42a of the inner shell 42 and the second part 54b of the secondary openings is present in the inner layer 42b of the inner shell 42, and each secondary cavities 52 is connected to a secondary opening of the first part of the secondary openings 54a, which is then further connected to a secondary opening of the second part of the secondary openings 54b, which is then connectable to the removal means 60 in the transferring zone B and optionally to the vacuum system 71A in the receiving zone.

As set out above, the moving endless surface 40 may have a first and optionally a second lateral edge zones 45a, 45b (each extending in MD) on one or either side of a central zone 46 (extending in MD) and then, the first part 54a of the secondary openings may be present in the central zone 46 and in connected to (and for example in contact with) the secondary cavities 52 in the central zone 46, and the second part of the secondary openings 54b may be present in one or both lateral edge zones, the lateral edge zones being for example also free of the primary cavities 51 and/or free of primary openings, and optionally free of secondary cavities 52.

Thus, in some embodiments herein, and for example shown in FIGS. 5, 6a and 6b, the primary cavities 51 and the secondary cavities 52 are present only in the central zone 46, the primary openings 53 are present only in the central zone 46, and the secondary openings of the first part of the secondary openings 54a are present only in the central zone 46, and whereby the secondary openings of the second part of the secondary openings 54b are present only in one or both lateral edge zones 45a, 45b, and whereby each of the secondary openings of the first part of the secondary openings 54a is connected to a secondary opening of the second part of the secondary openings 54b, which is connectable to the removal means 60 in the transferring zone (B, but not connectable to the vacuum system 71B in the transferring zone B, and that is optionally connectable to the vacuum system 71A in the receiving zone. For example the secondary opening(s) of the first part of secondary openings 54a are positioned in a row 56; in CD or multitude of rows in the central zone 46, and that each of the openings 54a is connected to one or more secondary cavities of the second part 54b that is positioned in the same CD row 56, but in the lateral edge zone(s) (and not in the central zone 46), as shown for example in the FIGS. 6a and 6b.

It should be understood that the secondary openings 54 or 54a, but also or alternatively the primary opening 53, may alternatively be CD-extending channel(s) in the inner shell 42 (not shown in the Figures).

The gas (e.g. air) inlet system, (e.g. forming part of removal means 60 herein, and/or present in the releasing zone C, and having for example an gas inlet 72b) of the apparatus 1 and method herein may be any system suitable to introduce/blow a gas with an adjustable/controlled pressure through a multitude of (primary and secondary) openings/cavities. In some embodiments, the apparatus 1 has an air chamber in close proximity or adjacent to the moving surface, e.g. adjacent the inner layer 42a thereof, in the releasing zone C, and optionally in the lateral edge zones of the transferring zone B.

In some embodiments herein, the gas (air) is blown through the primary openings 53 and cavities when moving through the releasing zone C, but substantially not through the secondary cavities 52 and secondary openings. Then, the gas (air) chamber may be present only in the central zone 46 of the releasing zone C, and not in the lateral edge zones.

Figure 3:
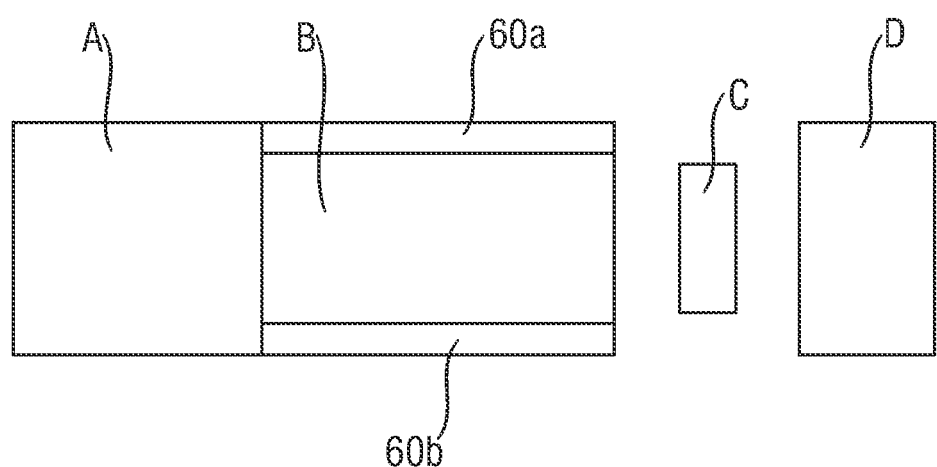
FIG. 3 is a schematic view of the zones of a moving endless surface at a moment in time.

Thus, as shown in FIG. 3 for example, the vacuum chamber in the transfer zone 71B may be adjacent only the central zone 46 of the moving endless surface 40 or inner layer thereof; the vacuum chamber in the receiving zone 71A may be adjacent the central zone 46 and edge zones 45 a, b of the moving endless surface 40 or inner layer thereof; the gas-inlet chamber (s) 60a, b in the transfer zone 71B may be adjacent only the edge zone or zones 45 a, b of the moving endless surface 40 or inner layer thereof; the gas-inlet chamber 71C in the releasing zone may be adjacent only the central zone 46 of the moving endless surface 40 or inner layer thereof; or alternatively adjacent the central and edge zone(s).

In some embodiments herein, the apparatus 1 and/or method herein may comprise one or more further zones or method steps, respectively, for cleaning the cavities and/or the screen when present. This zone(s) or step(s) may follow the release step/zone C, if present. For the optional cleaning zone D, optionally E or step, the apparatus may have a gas-inlet system/chamber or the method may have a gas (air) blowing step, of blowing a gas (air) through some or all (typically all) of the primary, and/or secondary cavities e.g. via the primary and/or secondary openings, or part thereof, using a gas-inlet connection 72b. For example, a gas (air) may be blown through the primary openings 53 and the secondary openings, or the second part thereof, and then through the optional screen and through the cavities. This ensures that any residual solid material is removed from the cavities and/or from the optional screen, or from the moving surface as a whole (prior to receiving solid material in the next cycle of the apparatus 1/method.

This may have a higher pressure than the gas (air) used in the releasing zone C/release step, if present.

The apparatus may comprise additional components or units, as described below for example; the method may comprise additional method steps, as described below for example; one advantageous step may comprise recycling the second portion of the solid material 100b back into the receiving zone/step A, e.g. to the hopper, with the removal means and additional recycling steps/components. The apparatus/method may in addition comprise a scraper blade or doctor blade to remove excess solid material from the moving endless surface 40 in the receiving zone/step.

Another advantageous additional apparatus component/method step, is the use of a 3-D plate 10 that guides the solid material into the cavities during the receiving step A and/or that keeps the first portion of the solid material 100A in the primary cavities during transfer in transfer zone B.

The solid material 100a may be transferred by the moving endless surface 40 to a further process step, to a further apparatus component or unit, or to a further moving surface or substrate; it may be transferred to for example a second moving (e.g. endless) surface 80. The solid material 100a transfers for example from the moving endless surface 40 (i.e. the primary cavities 51 thereof) to the further surface (e.g. substrate) 80 in the releasing zone C. The further surface 80 may be a belt or drum, for example, or may be a moving substrate for example, such as a film (e.g. film web) or such as, in some embodiments herein, a nonwoven (e.g. nonwoven web). For example, the further surface may be a substrate carried on a moving endless surface 80 such as a belt or a drum. In one embodiment herein, the further moving endless surface 80 is a substrate carried on moving endless support, such as a roll, drum, or belt. This support may comprise vacuum means and openings, through which the vacuum can be applied to the substrate, to retain the substrate on the support. The substrate/surface may have the same surface speed as the first moving endless surface 40, or it may have a different speed. In one embodiment, it has a speed of at least 1000 part per minute and/or a speed of at least 4.5 m/s, or at least 6 m/s, or at least 8 m/s.

In one embodiment, the moving endless surface 40 moves, e.g. rotates, and the further surface 80 is positioned (for example, placed) substantially under the first moving endless surface 40 so that the solid material 100a can be released to the surface/substrate to by gravity. The releasing zone C may thus be parallel or approximately parallel to the line of gravity, or under an angle with the line of gravity of from 60° to −60°, or from 30° to −30°.

In one embodiment, the further moving endless surface 80 comprises a web of a substrate with another component, such as another or further solid material 100; and/or such as an adhesive, e.g. to, at least partially, adhere the solid material 80 to the substrate. To better allow vacuum to be applied on the substrate with adhesive, the adhesive may be applied in a pattern, whereby parts of the substrate do not comprise adhesive and parts of the substrate do comprise adhesive. The pattern may correspond to the pattern of the primary cavities 51 of the moving endless surface 40.

After transfer of the material 100a to the moving substrate/surface 80, the surface/substrate may move the solid material 100a to further additional method step(s) or apparatus unit(s), to apply further materials to the solid material 100a and/or the substrate. This may include one or further adhesive(s), for example applied by a further (downstream) adhesive unit, and/or a further substrate, applied for example by a further (downstream) substrate application unit, e.g. a rotating support carrying a further substrate, and/or a cutting unit etc.

In one embodiment, the substrate with the solid material 100a moves to a unit that applies an adhesive material, and/or a thermoplastic material and/or an adhesive thermoplastic material, for example in fibrous form, to cover the solid material 100a, or part thereof. In another or additional embodiment, the substrate with solid material moves to a unit that applies a further substrate onto the material 100a, or optionally onto the adhesive and/or thermoplastic and/or thermoplastic adhesive material.

The further substrate may comprise adhesive on the side that contacts the solid material 100a (or optionally the thermoplastic and/or adhesive and/or thermoplastic adhesive material), to better adhere the substrate to the solid material 100a. In one embodiment, the substrate with solid material (e.g. as a layer) is moved to a further unit, where a second substrate with solid material 100a (e.g. as a layer), e.g. made by an apparatus 1 in the manner described herein, is superposed thereon, for example such that substrate and further substrate sandwich the solid material 100a, e.g. the two solid material "layers"." In one embodiment, the substrate with solid material made with an apparatus 1 disclosed herein and/or the methods disclosed herein, is moved to a further apparatus 1 or method disclosed herein, that transfers further solid material 100a onto the substrate with solid material (optionally onto the thermoplastic and/or adhesive and/or thermoplastic adhesive material).

The resulting substrate with solid material may thus be a web of articles (absorbent core or precursors thereof) herein (optionally combined with any of the further materials described above) and it may then move to a cutting unit, that cuts the substrate with solid material into individual articles, e.g. absorbent cores for absorbent articles, or precursors therefore. Such absorbent cores or partial absorbent articles may then be combined with further absorbent article components, described herein below, to form a final absorbent article.

The substrate may be joined to itself to or to an additional substrate (e.g. coversheet) by any means, for example by ultrasonic bonding, thermo-bonding or adhesive-bonding, e.g. for example sprayed adhesive bonding. The bonding region between the coversheet and the substrate, or may for example be at least 1%, or at least 2%, or for example at least 5%, but for example not more than 50% or no more than 30% of the surface area of the substrate. Suitably, the bonding region comprises essentially no solid material 100a.

As mentioned above, an adhesive, and/or thermoplastic or thermoplastic adhesive material may serve to at least partially cover and at least partially immobilize the solid, e.g. particulate, material 100a, for example an adhesive and/or thermoplastic or thermoplastic adhesive material in fibrous form, e.g. fibrous layer which is at least partially in contact with the solid material 100a and optionally partially in contact with the substrate. The thermoplastic material may be a hot melt adhesive material. In accordance with certain embodiments, the thermoplastic (adhesive) material may comprise a single thermoplastic polymer or a blend of thermoplastic polymers, having for example a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. The thermoplastic polymer may have a molecular weight ($M_w$) of more than 10,000 Da and a glass transition temperature ($T_g$) usually below room temperature or −6° C.<$T_g$<16° C. In certain embodiments, typical concentrations of the polymer in a hot melt are in the range of about 20% to about 40% by weight. In certain embodiments, thermoplastic polymers may be water insensitive. Illustrative polymers are (styrenic) block copolymers including A-B-A triblock structures, A-B diblock structures and $(A-B)_n$ radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of $C_2$ to $C_8$ alpha olefins. In illustrative embodiments, the tackifying resin has typically a $M_W$ below 5,000 Da and a $T_g$ usually above room temperature, typical concentrations of the resin in a hot melt are in the range of about 30% to about 60%, and the plasticizer has a low $M_W$ of typically less than 1,000 Da and a $T_g$ below room temperature, with a typical concentration of about 0% to about 15%.

In certain embodiments, the thermoplastic (adhesive) material may be in the form of fibers of an average thickness of about 1 µm to about 50 µm or about 1 µm to about 35 µm and an average length of about 5 mm to about 50 mm or about 5 mm to about 30 mm.

The cover layer may comprise the same material as the substrate, or may comprise a different material. In certain embodiments, suitable materials for the cover layer are the non-woven materials, useful for the substrate.

The present disclosure also relates to a method employing the steps, apparatus 1 or components thereof, described above.

Some embodiments of the disclosure, thus relates to a method for receiving, transferring and releasing solid material 100 using the apparatus 1 as described herein.

Alternatively, or in addition, the disclosure relates to a method for receiving with a moving endless surface 40 solid material 100 from a feeder, transferring the solid material with the moving surface and optionally releasing the solid material from the moving surface, e.g. to a further moving surface 80, the method comprising:

(a) receiving a first portion 100a of the solid material in primary cavities 51, the moving endless surface, and a second portion of the solid material in secondary cavities (52) of the moving endless surface;

(b) optionally applying a vacuum during (a) onto the primary and secondary cavities;

(c) moving the moving endless surface toward a further moving surface, while applying a vacuum onto only the primary cavities 51 and the first portion 100a of the solid material therein, and not onto the secondary cavities and the second portion 100b of solid material therein, thereby transferring the first portion 100a of the solid material in the primary cavities 51, to the further moving surface, and not the second portion 100b of the solid material, (d) removing the second portion 100b of the solid material from the secondary cavities 51 with a removal means 60; and (e) optionally releasing the first portion 100a of the solid material, for example to the further moving surface 80, by applying positive air pressure onto the primary cavities 51 and the first portion of the solid material 100a therein.

Thus, any of the above described features of the apparatus 1 and functions and method steps described herein apply the method of the disclosure.

The method and apparatus 1 herein may produce for example at least 800 parts per minute (ppm) or at least 1000 ppm, or at least 1100 ppm or at least 1200 ppm; the "parts" being the individual structures described herein, e.g. for example tablets, pouches, capsules, absorbent structures (cores) etc.

The moving endless surface 40 may have for example a surface speed of at least 2.0 m/s, or at least 3 m/s or at least 4.5 m/s, or at least 6.0 m/s, or at least 7.0 m/s, or at least 7 m/s. Alternatively, or in addition, the first surface area may have a speed defined by parts per minute, of for example at least 800 parts per minute, or at least 1000 parts per minute.

The method herein may be useful to make individual articles, such as capsules with solid material 100, tablets with the solid material 100, pouches with solid material 100; it may be particularly useful to make absorbent cores (including: a web thereof that may then be divided, e.g. cut, into individual absorbent cores), whereby the solid material 100 is an solid absorbent material, e.g. for example particulate AGM, for example with a mass median particle size of from 150 µm to 1000 µm, or from 200 µm or 300 µm to 700 µm.

The method may comprise adding a thermoplastic material, and/or adhesive material and/or thermoplastic adhesive material to the substrate 110 prior to transfer of the solid material 100 and/or to the solid material 100 and/or substrate 110 after the transfer, and/or the step to add further substrate(s) or covering sheet(s) and/or to fold the substrate 110 and close the substrate 110 over the solid material 100 and/or the step to add a further substrate with solid material 100 as described above.

The absorbent cores producible with the apparatus/method herein are typically for acquisition and/or storage of liquids (such as urine, blood) for absorbent articles, or precursors thereof, or partial absorbent articles.

"Absorbent article" refers to devices that can absorb and contain body exudates, and, more specifically, refers to devices that are placed against or in proximity to the body of the wearer to absorb and contain the various exudates discharged from the body. Absorbent articles may include diapers, including fastenable diapers and (refastenable) training pants; adult incontinence undergarments (pads, diapers) feminine hygiene products (sanitary napkins, panty-liners), breast pads, care mats, bibs, wound dressing products, and the like. "Diaper" refers to an absorbent article generally worn by infants and incontinent persons about the lower torso so as to encircle the waist and legs of the wearer and that is specifically adapted to receive and contain urinary and fecal matter. As used herein, the term "body fluids" or "body exudates" includes, but is not limited to, urine, blood, vaginal discharges, breast milk, sweat, and fecal matter.

The absorbent core is typically sandwiched between at least a backsheet and a topsheet. Absorbent articles herein may comprise a topsheet, facing the wearer in use, for example a nonwoven sheet, and/or an apertured sheet, including apertured formed films, as known in the art, and a backsheet, an absorbent core, having optionally a core coversheet facing the wearer in use. The backsheet may be liquid impervious, as known in the art. In some embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind., and sold under the trade names X15306, X10962 and X10964. The backsheet, or any portion thereof, may be elastically extendable in one or more directions. The backsheet may be attached or joined to a topsheet, the absorbent core, or any other element of the diaper by any attachment means known in the art.

The absorbent core, and optionally the absorbent article, may be "substantially cellulose free which means herein that it contains less than 10% by weight cellulosic fibers, or less than 5% cellulosic fibers, or less than 1% cellulosic fibers, or no cellulosic fibers.

In certain embodiments, the absorbent core herein may comprise an absorbent core content (so excluding the substrate or core cover or core wrap) of the particulate absorbent (polymeric) material (AGM) and a further material, such as the thermoplastic adhesive material; the weight ratio of the AGM to the further material may be at least 2:1, and of example up to 200:1, or for example at least 5:1 or at least 10:1 or at least 20:1.

Diapers herein may comprise leg cuffs and/or barrier cuffs; the article then typically has a pair of opposing side flaps and/or leg and/or barrier cuffs, each of a pair being positioned adjacent one longitudinal side of the absorbent core, and extending longitudinally along the core, and typically being mirror images of one another in the Y-axis (in MD) of the article; if leg cuffs and barrier cuffs are present, then each leg cuffs is typically positioned outwardly from a barrier cuff. The cuffs may extend longitudinally along at least 70% of the length of the article. The cuff(s) may have a free longitudinal edge that can be positioned out of the X-Y plane (longitudinal/transverse directions) of the article, i.e. in the Z-direction. The side flaps or cuffs of a pair may be mirror images of one another in the Y-axis (longitudinal axis; MD axis) of the article. The cuffs may comprise elastic material.

The diapers herein may comprise a waistband, or for example a front waistband and back waist band, which may comprise elastic material.

The diaper may comprise side panels, or so-called ear panels. The diaper may comprise fastening means, to fasten the front and back, e.g. the front and back waistband. Illustrative fastening systems comprise fastening tabs and landing zones, wherein the fastening tabs are attached or joined to the back region of the diaper and the landing zones are part of the front region of the diaper.

The absorbent article may also include a sub-layer disposed between the topsheet and the absorbent core, capable of accepting, and distributing and/or immobilizing bodily exudates. Suitable sublayers include acquisition layers, surge layers and or fecal material storage layers, as known in the art.

The absorbent article herein may comprise in addition one or more side flaps or cuffs. The topsheet or cuffs or side flaps may comprise a skin care composition or lotion or powder, known in the art, panels, including those described in U.S. Pat. Nos. 5,607,760; 5,609,587; 5,635,191; and 5,643,588.

The (absorbent) core formed herein comprises in one embodiment a substrate with the solid material, whereby the substrate 110 is C-folded to enclose the solid material 100. In other words, the solid material 100 may be deposited unto the substrate 110 and the substrate 110 may then be folded to cover the solid material 100. Alternatively, or in addition, a separate sheet material, or cover sheet, may be placed over the solid material 100 after it is deposited onto the substrate 110, to cover the solid material 100. Such a coversheet may be any of the material described herein above as substrate 110 material, e.g. a nonwoven sheet or web.

Alternatively, or in addition, two or more of the substrates with solid material deposited thereon may be produced and placed onto one another, to cover one another. Hereby, an additional coversheet may be placed first onto the solid material 100 on the substrate, and then a further substrate with solid material may be placed thereon, typically such that the latter solid material 100 contacts the coversheet.

Documents referred to herein are hereby incorporated by reference. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. An apparatus comprising:
   a receiving zone for receiving solid material,
   a transferring zone for transferring a first portion of said solid material;
   optionally, a releasing zone for releasing said first portion of said solid material;
   a moving endless surface, moving through said receiving zone, transferring zone and releasing zone of said apparatus and said moving endless surface comprising an outer shell with a multitude of primary cavities for receiving a first portion of said solid material and with a multitude of secondary cavities for receiving a second portion of said solid material;
   a vacuum system in said transferring zone for retention of said first portion of solid material during transfer, wherein said primary cavities are connectable to said vacuum system of said transferring zone, and said secondary cavities are not connectable to said vacuum system of said transferring zone; and
   a removal means in said transferring zone for removing in the transferring zone the second portion of said solid material from said secondary cavities.

2. The apparatus of claim 1, wherein each primary cavity defines an open surface area and each secondary cavity defines an open surface area, and the ratio of the total open surface area of the primary cavities to the total open surface area of the secondary cavities 52 is from 50:1 to 1:10.

3. The apparatus of claim 1, wherein each primary cavities has a maximum depth of at least 1 mm and each secondary cavities has a maximum cavity depth of at least 1 mm, and the total volume of said primary cavities to the total volume of the secondary cavities is from 50:1 to 1:10.

4. The apparatus of claim 1, wherein said receiving zone has a vacuum system and said primary cavities and said secondary cavities are connectable to said vacuum system of said receiving zone.

5. The apparatus of claim 1, wherein aid removal means comprises a gas-inlet system, and wherein the secondary cavities each have a base surface area and wherein in said transferring zone, or part thereof, said base surface area of the secondary cavities, or part thereof, are connectable to said gas-inlet system, which blows a gas through said base surface areas and through said cavities, to remove said second part of said solid material from said secondary cavities.

6. The apparatus of claim 1, wherein said moving endless surface has an outer shell, comprising said primary and secondary cavities; and an inner shell comprising a multitude of primary openings and a multitude of secondary openings and each of said primary cavities is connected to a primary opening, and via said openings connectable to said vacuum system; and each of said secondary cavities is connected to a secondary opening, or a first part thereof, connectable, optionally via a second part of said secondary openings to said removal means, in said transferring zone, and optionally to said vacuum system in said receiving zone.

7. The apparatus of claim 6, wherein said inner shell has a first outer layer and an second inner layer, wherein said first part of said secondary openings or all of said secondary openings is present in said first outer layer of said inner shell and said second part of said secondary openings is present in said inner layer of said inner shell, and each secondary cavities is connected to a secondary openings of said first part of said secondary openings, which is further connected to a secondary opening of said second part of said secondary openings, which is connectable to said removal means of the transferring zone and optionally to said vacuum system of the receiving zone.

8. The apparatus of claim 7, wherein said moving endless surface has a first and second lateral edge zones each extending in MD and therein between a central zone extending in MD, wherein said primary cavities and said secondary cavities are present only in said central zone, and said primary openings are present only in said central zone, and said secondary openings of said first part of said secondary openings are present only in said central zone, and wherein said secondary openings of said second part of said secondary openings are present only in one or both lateral edge zones, and wherein each of said secondary openings of said first part of the secondary openings is connected to a secondary opening of said second part of said secondary openings 54b, which is connectable to said removal means of the transferring zone, but not connectable to said vacuum system of said transferring zone, and that is optionally connectable to said vacuum system of the receiving zone.

9. The apparatus of claim 1, wherein said moving endless surface moving in MD comprises said primary cavities and secondary cavities in the form of a pattern of a multitude of rows of primary cavities, each row extending in CD, perpendicular to MD, and a multitude of rows of secondary cavities each extending in CD, perpendicular to MD; and said moving endless surface comprises said primary openings and secondary openings or only said first part thereof, in the form of a pattern of a multitude of rows of primary openings each row extending in CD, perpendicular to MD and a multitude of rows of secondary cavities only said first part thereof each extending in CD, perpendicular to MD.

10. The apparatus of claim 9, wherein at least 30% of said rows of said primary cavities and at least 30% of said rows of said secondary cavities are alternating primary cavities row and secondary cavities rows, and at least at least 30% of said rows of said primary openings and at least 30% of said rows of said secondary openings are alternating primary and secondary openings rows.

11. The apparatus of claim 1, wherein said moving endless surface has one or more areas extending in MD and CD and comprising a multitude of rows of said secondary cavities and being free of primary cavities.

12. The apparatus of claim 1, having a releasing zone, comprising a gas-inlet system, for example an air-pressure application means, for applying pressurized air through said primary openings and primary cavities onto said first portion of said solid material, and optionally through said secondary openings and through said secondary cavities.

13. The apparatus of claim 1, wherein said removal means includes means for recycling said second portion of said solid material to said receiving zone of said apparatus.

14. A method comprising:
  receiving, transferring, and releasing solid material using the apparatus of claim 1.

15. A method for receiving, transferring, and releasing a solid material from a feeder with a moving endless surface, said method comprising:
  (a) receiving a first portion of said solid material in primary cavities of said moving endless surface, and a second portion of said solid material in secondary cavities of said moving endless surface;
  (b) optionally applying during said step (a) a vacuum onto said primary and secondary cavities;
  (c) moving said moving endless surface to said further moving surface, while applying a vacuum to said primary cavities and said first portion of said solid material therein, and not to said secondary cavities and said second portion of solid material therein, thereby transferring said first portion of said solid material in said primary cavities, to said further moving surface, and not said second portion of said solid material;
  (d) removing said second portion of said solid material from said secondary cavities with a removal means; and
  (e) optionally releasing said first portion of said solid material, optionally to a further moving surface.

16. The method of claim 15, wherein (a) through (e) are performed using the apparatus of claim 1.

17. The method of claim 15, wherein said method is a continuous method, wherein (a) through (e) form a cycle that is continuously repeated, and wherein in (d) during a given cycle the removed second portion of said solid material is recycled to (a) of a subsequent cycle.

18. The method of claim 17, wherein from 10% to 60% of the total amount of said solid material is said second portion.

19. The method of claim 15, wherein said moving endless surface has a surface speed of at least at least 1000 parts per minute and a surface speed of at least 4.5 m/s.

20. The method of claim 15, wherein said solid material comprises particles, and said particles have a mass median particle size of from 100 μm to 1000 μm.

* * * * *